(12) United States Patent
Rosenberg

(10) Patent No.: US 7,314,326 B2
(45) Date of Patent: Jan. 1, 2008

(54) DEVICE AND METHOD FOR TREATING PATHOLOGICALLY AFFECTED SKIN

(75) Inventor: Lior Rosenberg, Omer (IL)

(73) Assignee: 4-Med, Kfar-Sava (IL)

( * ) Notice: Subject to any disclaimer, the term of this patent is extended or adjusted under 35 U.S.C. 154(b) by 401 days.

(21) Appl. No.: 10/484,285

(22) PCT Filed: Jun. 13, 2002

(86) PCT No.: PCT/IL02/00591

§ 371 (c)(1),
(2), (4) Date: Aug. 9, 2004

(87) PCT Pub. No.: WO03/008033

PCT Pub. Date: Jan. 30, 2003

(65) Prior Publication Data

US 2004/0265040 A1    Dec. 30, 2004

(30) Foreign Application Priority Data

Jul. 19, 2001 (IL) .................................. 144463

(51) Int. Cl.
*B43K 5/00* (2006.01)
*A61M 35/00* (2006.01)
(52) U.S. Cl. .................... 401/204; 401/203; 604/2
(58) Field of Classification Search ........ 401/203–207; 604/1, 2
See application file for complete search history.

(56) References Cited

U.S. PATENT DOCUMENTS

| | | | | |
|---|---|---|---|---|
| 1,358,733 A | * | 11/1920 | Heine | ......................... 401/204 |
| 2,904,809 A | * | 9/1959 | Clayson | ...................... 401/136 |
| 3,000,040 A | * | 9/1961 | Carlson | ...................... 401/198 |
| 3,402,009 A | | 9/1968 | Sawyer | |
| 4,225,254 A | | 9/1980 | Holberg et al. | |
| 4,330,220 A | | 5/1982 | Schaar et al. | |
| 4,451,164 A | | 5/1984 | Roberts, Jr. | |
| 4,507,111 A | | 3/1985 | Gordon et al. | |
| 4,578,055 A | * | 3/1986 | Fischer | .......................... 604/2 |
| 4,780,361 A | | 10/1988 | Schlein | |
| 4,889,441 A | * | 12/1989 | Tice | ........................... 401/131 |
| 5,154,524 A | * | 10/1992 | Anderson | .................... 401/203 |

* cited by examiner

*Primary Examiner*—David J. Walczak
(74) *Attorney, Agent, or Firm*—AlphaPatent Associates Ltd.; Daniel J. Swirsky

(57) ABSTRACT

Device for treating pathological conditions of skin surfaces, which comprises a main component that includes a body and a contact layer superimposed to one another, wherein the body is porous to provide storage capacity for liquid medicament fed to it and permeable for transmitting the medicament to the contact layer by compression or capillarity or both. The contact layer is also porous for transmitting the medicament received from the body to the skin surface being treated and has a mildly or strongly abrasive outer surface for removing damaged surface skin tissue. The device also comprises a delivery apparatus for feeding liquid medicament to the body of the main component and, an optional storage container for the liquid medicament.

14 Claims, 3 Drawing Sheets

DEVICE AND METHOD FOR TREATING PATHOLOGICALLY AFFECTED SKIN

FIELD OF THE INVENTION

This invention relates to a device for the treatment of pathological conditions of the skin, particularly but not exclusively, burns or other cutaneous traumas. This invention also relates to the method that is carried out by means of said device.

BACKGROUND OF THE INVENTION

Pathological skin conditions, particularly traumatic ones, often require a preliminary treatment to clean and prepare the affected area for a main following treatment, whether by means of medicaments or by mechanical/surgical means. A frequent case of such conditions is the presence of burns, and therefore, reference will be made to burns in this specification and claims. However, this should not be construed as a limitation, since the device and the method of this invention can be applied to other pathological skin conditions. Such conditions may be acute such as any cutaneous trauma, open wounds, abrasions trauma, foreign bodies (shrapnels, explosives, gravel etc.), avulsion injury, or may be chronic such as macerating wounds and sores (pressure, diabetics, leg, vascular etc.). Another condition is when the skin is covered with foreign material, such as dirt, oils paints and grease etc., that should be removed prior to the beginning of any treatment. For the main treatment, by medicaments or by surgical means, to be completely successful, it is generally necessary to remove firstly most or all of the damaged tissue and foreign materials that may be present. There are no efficient devices or methods for such a removal or cleaning to be carried out in preparation for a definitive treatment. Treatments by mechanical action and application of medicaments are generally carried out successively or intermittently and with unsatisfactory results, both as to the times and conditions of the treatments and as to their results. The present state of the art is the use of sterile gauze or other sterile fibrous and absorbing material soaked in large quantities of sterile saline with or without additives such as soap, peroxide, antiseptiocs, etc. This is done usually by opening a large sterile container, into which several liters of saline are poured. Into this solution, several packs of sterile gauze (4×4) or other large such dressing, are immersed. The wet gauzes are used for cleaning, are prepared for a second use by squeezing out the scraped material and saline, usually into the container. In many case the same container is used, while the contaminated saline is reused to continue the cleaning. Therefore, the quality of the saline in the container deteriorates and it has to be replaced. Obviously, both the container and the new introduced saline become contaminated. The drawbacks of the traditional methods are that it:
a. is non-hygienic
b. requires a large sterile container
c. requires a large amount of sterile gauze
d. demands large volume of sterile saline.

Additionally, the scraping surface of the gauze may be too soft to either remove imbedded foreign materials, or loosen or detach tissues or dirt.

In conclusion, the known method is not effective and is relatively costly.

It is therefore a purpose of this invention to provide, for the first time in the art, a device for the preliminary treatment of damaged skin tissue, particularly skin tissue that is affected by burns.

It is another purpose of this invention to provide a device and a method by which preliminary removal of damaged tissues and application of medicaments can be carried out concurrently without mutual interference.

It is a further purpose of this invention to provide a device for carrying out the aforesaid purposes that is very simple and economical and that comprises components that are already known per se and that most of them are already available.

It is still a further purpose of the invention to provide means for carrying out the aforesaid purposes, which make use of devices and methods already known in the medical art for delivering treatment to a desired destination in the human body.

It is another purpose of this invention to provide a standard device and method by which the removal of material and damaged tissues will be standardized.

Other purposes and advantages of the invention will appear as the description proceeds.

SUMMARY OF THE INVENTION

The device of the invention comprises a main component that includes a body and two contact layers superimposed to one another, whereby the body is porous to provide storage capacity for liquid medicament fed to it and permeable for transmitting the medicament to the contact layer by compression or capillarity or both; and the contact layer is also porous for transmitting the medicament received from the body to the skin surface being treated and has a mildly or strongly abrasive outer surfaces for removing damaged surface skin tissue. The device of the invention further comprises a delivery apparatus for feeding liquid medicament to the said body of said main component, and, optionally, a storage container for said liquid medicament.

The aforesaid main component body is made of a sponge-like material, preferably a polymeric sponge. Said polymeric sponge can be made for example of cellulose, cotton, polyurethane foams, polyvinyl chloride (PVC), polyvinyl acetate (PVA) and the like. Polymeric sponges, and the manner of making them, are well known in the art. The sponges themselves are easily available for several purposes, e.g. hygienic ones. They comprise an elastic matrix and a system of intercommunicating pores. Their elasticity, both in terms of compressibility and of elastic recovery after compressive deformation, and their porosity, which determines their permeability and is related to their ability to retain liquid in their pores, may vary widely. Their elasticity depends mainly on the polymer of which they are made while their porosity can be controlled on the process of their manufacture. It also depends on the thickness of the body, which however need only be sufficient to permit the use of the device without any contact of the hand of the user with the skin surface being treated. Thicknesses from 5 to 10 cm. are usually satisfactory. Persons skilled in the art can easily choose sponges having the elasticity and porosity desired for a specific purpose, or choose the polymer and the manufacturing parameters to obtain the desired elasticity and porosity. Preferably, the elastic recovery after compressive deformation should be at least as high as that of natural sponges, while their porosity may be as high or higher than that of natural sponges, however these are only preferred features.

For example, PVA sponges are produced and sold by Sponge-King, advertising on Internet http://www.ocean-es.fr/~about.c heaptel/spingeking.htm, and by Kanebo, advertising on Internet http://www.shimaamerican.com./kanebopva.html. Cellulose viscose sponge is produced by Cellomeda OY of Finland, advertising on Internet http//www.abo.fi/~about.klonnqvi/prodinfo.html. Cotton sponged are sold for surgical purposes under the trademark Premium Americal.TM., as advertised on Internet http://www.americansurgicalsp.com/premium americot-.htm. The surface of the sponge may be used as one of the cleaning surfaces when a soft, rather delicate cleaning action is needed. The second contact layer should also be permeable and should have an abrasive surface, at least on the side thereof not superimposed, viz, not connected to the body. The elasticity of the contact layer is unimportant. At the limit, it could be uncompressible, but in practice it will have some compressibility, though preferably lower than that of the body. It is thinner than the body, since it need not retain liquid to a significant extent. Thicknesses from a few millimeters to 2 cm. are usually satisfactory. The abrasiveness of the contact layer should be sufficient to provide a debriding action, but not so high as to cause pain or debriding below the affected skin surface layer. The desired abrasiveness can be achieved by choosing a sufficiently rigid polymeric material or by inserting into the polymer mass an abrasive material, generally an amount of mineral, insoluble or only slightly soluble, salts. The abrasiveness should be suitable to the tasks for which the device is used. Certain skin conditions may require high degrees of abrasiveness and other conditions, low ones.

The apparatus for feeding liquid medicament to the main component body may be any apparatus known for a similar purpose. For instance, infusion bags and tubing sets, such as are used in hospitals for infusions, may be suitable. Essentially, such an apparatus may comprise a storage element, which may be simply a polymer bag or a bottle, which can be suspended as to deliver its contents by gravity through a suitable conduit. The conduit may terminate with a portion having a nozzle that can be inserted into an opening or a connector of the main component body. In view of the porosity of said body, it will become saturated with that liquid and deliver it to the contact layer, due to the pressure under which it is fed or by capillarity, or both. The apparatus for feeding liquid will preferably have a terminal nozzle that can be inserted in the sponge-like main component body of the device, the elasticity of said body providing a sufficiently liquid-tight connection between said body and said nozzle. Means for controlling and or varying the pressure and flow by which the liquid is fed to said body might be provided. A typical system is an infusion system comprising infusion tubing set that end with a luer-lock nozzle.

The invention further comprises a method of treating pathological conditions of skin surfaces, which comprises exerting a mild or stronger abrasive action on the affected surface while causing liquid medicament to be delivered to it. Said method is also applicable for sanitation purposes, to deliver not a medicament, but a cleaning and/or disinfecting liquid to a skin area that can benefit from such a treatment.

DETAILED DESCRIPTION OF PREFERRED EMBODIMENTS

Figure 1:
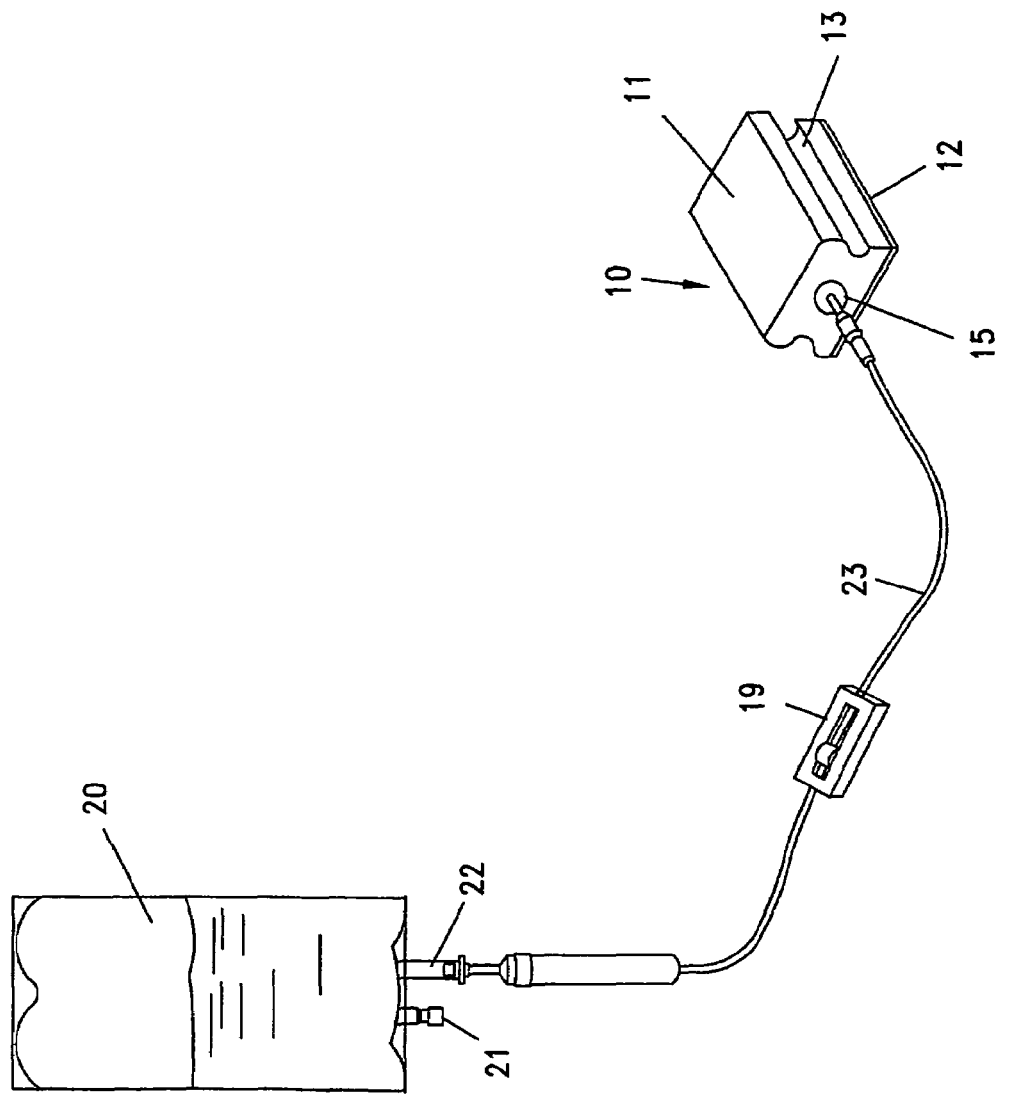
FIG. 1 there is schematic perspective representation of a device according to an embodiment of the invention.

In FIG. 1, a device according to the invention comprises a main component indicated at 10. Said main component comprises a sponge-like body 11 and, below it, a contact layer 12. In the embodiment shown in the drawings, body 11 has a rectangular longitudinal cross-section (see FIG. 2) and an approximately rectangular transverse cross-section (see FIG. 3) and it has longitudinal recesses 13 in its sides, as seen in FIGS. 1 and 3, to permit easy grasping and actuating of said main component.

The sponge body 11 is also provided with an opening 14 or seat (see FIG. 2) which is located in this embodiment at one end thereof, but may be located elsewhere, though it is preferred that it should be located at a relatively central point to facilitate distribution throughout said body 11 of the liquid fed to it. The terminal part of a nozzle 15 (see FIG. 1), through which the liquid medicament is fed to the device, can be inserted in opening or seat 14 and be held therein by the elastic compression exerted by said body 11.

In an embodiment having the shape illustrated, the dimensions may be, for example: width from 5 to 10 cm, length from 8 to 16 cm,. height of the body from 3 to 6 cm, and thickness of the abrasive contact layer 12 from 0.5 to 1.5 cm.

The invention also provides a method of preliminary treatment of pathological conditions of the skin which comprises a mildly abrasive and cleaning action of the effected skin means of a porous thick layer while delivering liquid medicaments to said layer and through it to the treated skin. The main body of the sponge, which is softer than the abrasive layer, can be used for more delicate cleaning, while the more abrasive surface, for removing matter that is most strongly attached to the skin.

In the embodiment of the invention shown, it is assumed that a simple infusion apparatus is used to fed liquid medicament to the device body, but this should not be construed as a limitation, as other apparatus may be used as long as it adapted to feed liquid medicament to the main component. In this embodiment, schematically illustrated in FIG. 1, the feeding apparatus comprises a plastic bag 20, suspended at a convenient height by means not shown, which has an inlet for introducing medicament into it, which inlet may be closed by means of a plug 21 or by other means, and also has an outlet 22 connected to a conduit 23 at the end of which the nozzle 15 is inserted. Along conduit 23 is inserted a regulating valve 19, such as used for infusion.

Figure 2:
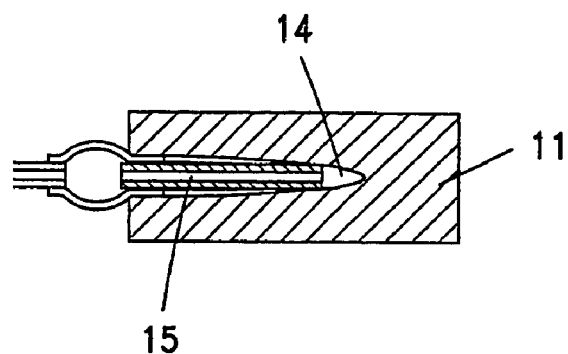
FIG. 2 is a longitudinal cross-section of the main component of the device.
Figure 3:
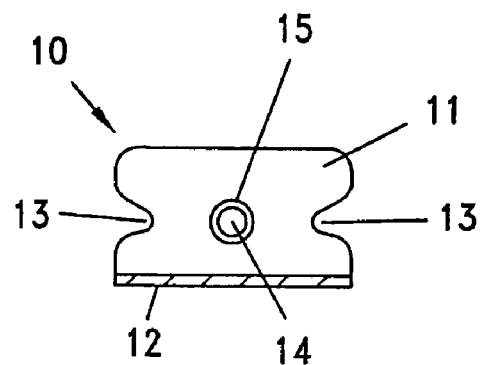
FIG. 3 is a transverse cross-section of said main component.
Figure 4:
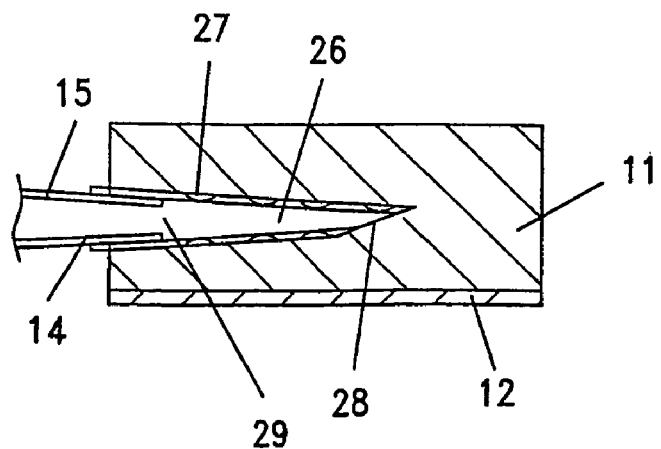
FIG. 4 is a longitudinal cross-section similar to FIG. 2, but showing a connector inserted into the main component.
Figure 5A:
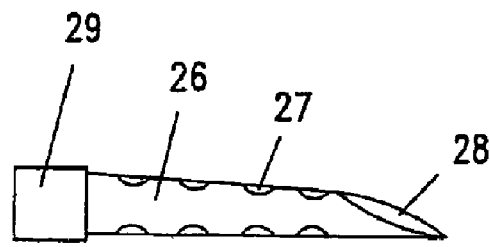
FIGS. 5a to 5e) illustrate various embodiments of the connector.
Figure 5B:
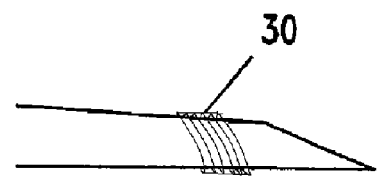
Figure 5C:
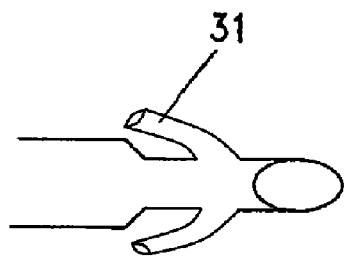
Figure 5D:
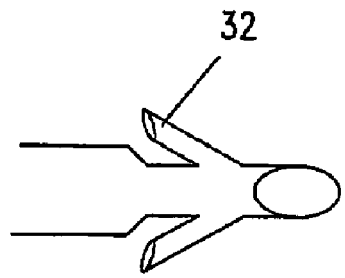
Figure 5E:
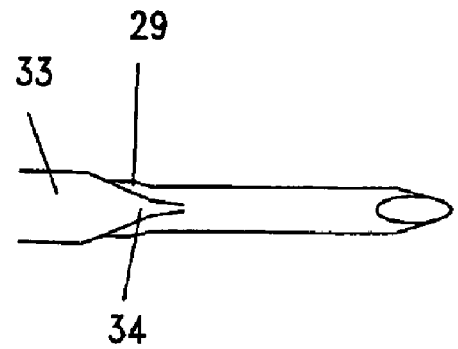

FIGS. 2-3 show the main soft sponge body 11, the abrasive layer 12, and the opening 14 in the main sponge body. FIG. 4 illustrates the same sponge body as in FIG. 2 but with perforated connector 26, which is inserted into the sponge. The perforated connector shown has a beveled, sharp distal end 28 for piercing the sponge, main tubular body 26 which is perforated at several points such as at 27, and a conical proximal end 29 to accommodate a luer-lock nozzle. The connector may have a flat screw thread 30 (FIG. 5b-d) that may allow the screwing of the tube into the sponge and prevent its pulling out. The connector with the sharp beveled end may be provided with one or two spikes or flaps like an arrowhead allowing stabbing it into the sponge and preventing its being pulled out accidentally (FIGS. 5c and 5d with spikes 31 and 32 respectively). The tube may be provided with one-way valve 33, which allows free flow of fluid, and prevents its back flow. This valve proximal opening is provided with a conical luer-lock inlet 34. When such a tubular connector is used, the sponge need not to have an opening 14, as in FIG. 2, since the connector will create its own seat when it is inserted.

Depending on the desired action, the upper surface of the body or the lower surface of the contact layer 12 may be pressed and rubbed against the skin of a person, a patient or anybody needing a skin treatment. Thus the device may be used for gently cleaning and cleansing the skin by rubbing the soft sponge surface of body 11 against the skin, moisturizing it by compressing the device; but for a stronger and deeper scraping or a debriding action, the more abrasive surface of contact layer 12 is used. In both cases, the amount of liquids used for moisturizing the skin is well controlled by the valve along the tubing and by squeezing the main body of the sponge. The soft surface of body 11 may be used for general cleaning, blister removal, etc. The abrasive surface of contact layer 12 may be used for mechanical debridement, foreign body removal and superficial cosmetic dermabrasion. For cleaning purposes a detergent liquid may be used, while for therapeutic purposes, a saline solution is used with any local medicament, such as antiseptic solution, antihistaminic solution, etc., that is suitable for the user for a specific condition.

While an embodiment of the invention been illustrated, this should not be construed as a limitation, since this invention may be carried into practice with many modifications and variations are without exceeding the scope of the claims.

The invention claimed is:

1. A device for treating pathological conditions of skin surfaces, comprising:
   i. a main component that includes a body and a contact layer superimposed to one another, wherein the body is porous to provide storage capacity for liquid medicament fed to it and permeable for transmitting the medicament to the contact layer by compression or capillarity or both; and the contact layer is also porous for transmitting the medicament received from the body to the skin surface being treated and has a mildly or strongly abrasive outer surface for removing damaged surface skin tissue, said main component having a shape that permits grasping; said main component further comprising a terminal part of a nozzle;
   ii. a storage container having an outlet, and
   iii. a delivery apparatus comprising a hose and a regulating valve, connecting said storage container outlet to sad main body terminal part for feeding liquid medicament from said storage container said main component;
   wherein said delivery apparatus, is adapted for inserting and firmly affixing to said main component to apply said liquid medicament to said damaged surface skin tissue in a manner controllable by said regulating valve, for any length of time while said liquid medicament in said container lasts.

2. The device of claim 1, wherein the body of the main component is made of sponge-like material.

3. The device of claim 1, wherein the sponge-like material is a polymeric sponge.

4. The device of claim 3, wherein the polymeric sponge is made of a material chosen from the group consisting of cellulose, cotton, polyurethane foams, polyvinyl chloride (PVC), and polyvinyl acetate (PVA).

5. The device of claim 1, wherein the body of the main component has a height or thickness from 5 to 10 cm. and the contact layer has a height or thickness from a few millimeters to 2 cm.

6. The device of claim 1, adaptable for feeding said liquid medicament to said main component body by gravity through suspending said storage container elevated with respect to said main component body.

7. The device of claim 6, further comprising means for controlling and or varying the pressure and flow by which the liquid is fed to the main component body.

8. The device of 6, wherein said storage container is an infusion apparatus which is replaceable with a full one when said storage container is emptied.

9. The device of claim 6, comprising a sharp perforated connecting tube with a lure-lock proximal opening inserted into the main component body.

10. The device of claim 9, wherein the connecting tube lure has a thread, flap(s) that prevent its pulling out from the main sponge block.

11. The device of claim 9, wherein the connecting tube has a one-way valve in its proximal opening to prevent back flow of fluids.

12. The device of claim 1 , the elasticity of said body is adapted for sufficiently liquid-tight connection between said body and said nozzle.

13. The device of claim 1, wherein the main component has a rectangular longitudinal cross-section and an approximately rectangular transverse cross-section.

14. Method of using the device of claim 1 for mild dermabrasion.

* * * * *